United States Patent [19]

Mayeux

[11] Patent Number: 5,558,129
[45] Date of Patent: *Sep. 24, 1996

[54] STREAM SELECTOR FOR PROCESS ANALYZER

[75] Inventor: Donald P. Mayeux, Prairieville, La.

[73] Assignee: Whitey Co., Highland Heights, Ohio

[*] Notice: The term of this patent shall not extend beyond the expiration date of Pat. No. 5,361,805.

[21] Appl. No.: 335,173

[22] Filed: Nov. 7, 1994

Related U.S. Application Data

[63] Continuation of Ser. No. 195,368, Feb. 14, 1994, Pat. No. 5,361,805, which is a continuation of Ser. No. 928,780, Aug. 13, 1992, Pat. No. 5,305,788.

[51] Int. Cl.$^6$ ..................................................... F16K 31/12
[52] U.S. Cl. ........................ 137/885; 137/343; 137/583; 137/881; 137/884
[58] Field of Search ............................... 137/885, 881, 137/884, 343, 583; 251/367

[56] References Cited

U.S. PATENT DOCUMENTS

| | | |
|---|---|---|
| 2,473,465 | 6/1949 | Betz . |
| 3,314,448 | 4/1967 | Wolff et al. . |
| 3,509,913 | 5/1970 | Lewis . |
| 4,687,017 | 8/1987 | Danko et al. . |
| 4,846,212 | 7/1989 | Scobie et al. . |
| 5,000,212 | 3/1991 | Tervo . |
| 5,170,659 | 12/1992 | Kemp . |

*Primary Examiner*—A. Michael Chambers
*Attorney, Agent, or Firm*—Fay, Sharpe, Beall, Fagan, Minnich & McKee

[57] ABSTRACT

A stream selector for a process analyzer. The stream selector includes a valve module having two block valves and a bleed valve. In a first mode, the block valves are closed and the bleed valve is open. In a second mode, the block valves are open and the bleed valve is closed. In a third mode, all of the valves are open, thus ensuring that the module is completely purged. A stream-selection valve manifold is made by joining two or more valve modules side by side to form a common outlet and a common passageway, thus ensuring that the manifold is completely purged. The stream selector also provides a single block-and-bleed valve module having a disposal passageway which establishes fluid communication between a vent compartment and an external area suitable for the safe disposal of sample fluids and compressed gas contained in the valve module. The flat-face sealing structure of each valve is very tolerant of scratching and/or irregularities in the sealing structure and of abrasive particulates which may be present in the sample fluid, even to minor structural damage to the sealing structure.

9 Claims, 7 Drawing Sheets

STREAM SELECTOR FOR PROCESS ANALYZER

REFERENCE TO PRIOR APPLICATION

This application is a continuation application of U.S. Ser. No. 08/195,368, filed Feb. 14, 1994, now U.S. Pat. No. 5,361,805, which is a continuation application of 07/928,780, filed on Aug. 13, 1992, now U.S. Pat. No. 5,305,788.

BACKGROUND OF THE INVENTION

The present invention relates to stream selection. More particularly, the present invention relates to the selection of sample streams being routed to a process analyzer.

It is common practice to utilize a single automated process analyzer for analyzing multiple sample streams. This significantly reduces the cost of analyzing, gas and liquid process streams in petrochemical plants, refineries and other process-related industries. The sample streams are generally transported near to an analyzer by tubing or piping. An automated valving manifold, usually electronically controlled, sequentially selects and diverts individual sample streams to the automated analyzer. This type of valving arrangement is generally referred to as a "stream-select manifold."

It is extremely important that sample-stream cross-contamination does not occur; i.e., absence of contamination of one sample stream by another in the sample stream selected for analysis. The most likely source of cross-contamination is from leaking "stream-select valves" in the stream-selection valving manifold.

Another common problem is the contamination of a stream selected for analysis by residual fluid from a previous sample stream. This is likely to occur in a common passageway between the valve manifold and the analyzer. Valve-manifold designs have either "dead volume," irregular passageways, or large internal volumes, which require longer period of sample flow (purging) before all residual fluid from a previously selected sample stream is removed. A common source of "difficult-to-purge" internal valve manifold volume is pipe fittings which provide an irregular internal surface. A common source of dead volume is the space between the block valve of a "non-selected" stream and the common sample fluid passage to an analyzer.

When longer sample-stream purge periods are required, it reduces the number of analyses which can be performed by an analyzer in a given period of time. This can increase the cost for analysis by requiring additional analyzers or otherwise negatively impact process adjustments based on current analysis.

Most important, however, is the increased volume of purged sample material which must be discarded. This also increases cost and presents a greater risk of contaminating the environment.

Valves utilized in stream-select manifolds for the most part were designed for ordinary pneumatic and hydraulic fluid-handling applications. Designs have been altered to some degree to accommodate stream-select manifold requirements. But few are designed exclusively for that purpose. Those which are designed primarily for stream selection are of the single block valve design, and are therefore prone to cross-contamination problems when even a slight leak develops.

Modular valve manifold arrangements are well known and in common service. These manifolds, however, are designed to facilitate the addition or removal of individual valves, and to reduce the number of tube and/or pipe fittings required. Their main purpose is to reduce space in pneumatic and hydraulic, not analytical, applications. Hence little consideration has been given to reducing internal volume and/or "dead" (unpurged) space, or the prevention of cross-contamination by residual fluids. Few if any provide double-block-and-bleed (DBB) protection from cross-contamination. Some manifold/valve designs even allow stacking of manifold modules to create a manifold of a desired length; however, the valves are a separate entity, and are attached to the manifold.

Another common problem with stream-selection valves is "fugitive emission" of sample fluids. This typically occurs when a valve stem seal fails. A metal bellows or diaphragm is frequently employed to seal the external actuation linkage to a valve's internal sealing mechanism. This arrangement, particularly when used in combination with a secondary packing, is very effective in reducing fugitive emission from valves. However, embrittlement of metal bellows or diaphragms, particularly in hydrogen-rich sample-stream service, and fatigue from repeated actuation, often causes premature stem-seal failures. Additionally, valves employing the bellows/diaphragm seal design are expensive, thus limiting their application. Furthermore, when the bellows or diaphragm fails, there can be an abrupt release of potentially flammable and/or toxic fluids to the surrounding environment. In summary, bellows/diaphragm valve stem seals are very effective during their normal service life, but have a severe and potentially unsafe failure mode.

Pneumatic actuation is often preferred in lieu of electric actuation for valves used in hazardous or electrically-classified environments. Current valve designs generally employ discrete pneumatic actuators usually mounted external to the valve with mechanical linkage through a seal to the internal valving mechanism. This arrangement results in a bulky design which takes up large amounts of valuable panel space. This is a particularly important consideration when considering the cost of providing panel space in a typical analyzer housing or environment. The large bulk also precludes close coupling of valves to minimize internal valve-manifold volume.

SUMMARY OF THE INVENTION

In general, the present invention in one aspect provides a valve module for a process analyzer. The module comprises a first block valve having a first opening, a second block valve having a second opening, and a bleed valve having a third opening. The first and second block valves are so constructed and arranged that both are closed simultaneously or both are open simultaneously. The block valves and the bleed valve are so constructed and arranged that, in a first mode, the block valves are closed and the bleed valve is open; in a second mode the block valves are open and the bleed valve is closed; and in a third mode, all of the valves are open, thereby ensuring that the module is completely purged.

The valve module further comprises flat-face sealing means for closing the valves by pressing the sealing means against a flat sealing surface, and for opening the valves by breaking contact between the sealing means and the flat sealing surface.

In a second aspect the present invention provides a stream-selection valve manifold. The valve manifold comprises first and second valve modules joined side by side to form a common outlet passageway and a common vent passageway. Each valve module includes two block valves and a bleed valve. The block valves are so constructed and arranged that both are closed simultaneously or both are open simultaneously. The three valves are so constructed and arranged that, in a first mode, the block valves are closed and the bleed valve is open; in a second mode, the block valves are open and the bleed valve is closed; and in a third mode, all three valves are open, thereby ensuring that the module is completely purged.

Each valve module further comprises flat-face sealing means for closing the valves by pressing the sealing means against a flat sealing surface, and for opening the valves by breaking contact between the sealing means and the flat sealing surface. One of the block valves communicates with an inlet passageway. The other block valve communicates with an outlet passageway. The bleed valve communicates with a vent passageway. Flow-through means hold the first and second valve modules in a fixed configuration wherein the outlet passageways of the first and second valve modules are aligned to form a common outlet passageway to and through the flow-through holding means, and the vent passageways from the first and second valve modules are aligned to form a common vent passageway, thereby ensuring that the manifold is completely purged.

In a third aspect, the invention provides a single block-and-bleed valve module. The module comprises a block valve, a sample-fluid compartment, a vent compartment, an internal pneumatic actuator, a sample-inlet first passageway, a sample-outlet second passageway, third and fourth passageways, first biasing means for closing the block valve, second biasing means for opening the valve, and a body having a cavity therein for housing the block valve, the sample-fluid compartment, the vent compartment, the pneumatic actuator, and the first, second, third, and fourth passageways.

The internal pneumatic actuator includes an actuator piston and an actuator compartment. The actuator compartment is constructed and arranged to receive compressed gas from an external source.

The first biasing means close the block valve by urging the piston in a first direction. The second biasing means, which include a compressed gas, open the valve by urging the piston in a second direction.

The block valve is so constructed and arranged that, when closed, fluid communication is blocked between the inlet passageway and the sample-fluid compartment; when open, the inlet passageway, the sample-fluid compartment, and the outlet passageway are in fluid communication.

The inlet passageway provides means for fluid communication from the external environment to the sample-fluid compartment. The outlet passageway provides means for fluid communication from the sample-fluid compartment to the external environment. The third passageway provides means for introducing a compressed gas into the actuator compartment. The fourth passageway provides means for fluid communication between the vent compartment and an external area suitable for the safe disposal of fluids contained within the valve module. The pressure within the vent compartment and the fourth passageway is normally maintained at a level equal to or lower than that of the sample-fluid compartment, the sample-inlet passageway, the sample-outlet passageway, and the actuator compartment, in order to prevent fugitive emission of the sample fluid or of the compressed gas from the module into unprotected areas of the external environment.

DETAILED DESCRIPTION OF THE INVENTION

Figure 1:
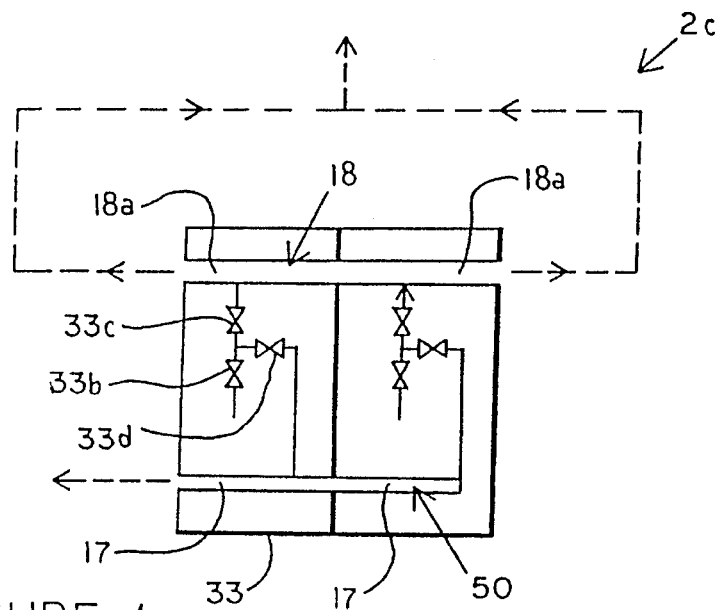
FIG. 1 is a schematic representation of a second embodiment of a stream-selection valve manifold for a process analyzer, made in accordance with the principles of the present invention.

The present invention, in a first embodiment (FIG. 3), provides a valve module 33 for a process analyzer. The module 33 comprises an internal pneumatic actuator, an inlet block valve 33b, an outlet block valve 33c, and a bleed valve 33d. The two block valves 33b, 33c are constructed and arranged so that both are closed or both are open simultaneously. The bleed valve 33d is constructed and arranged so that when the block valves 33b, 33c are open, the bleed valve 33d is closed; when the block valves 33b, 33c are closed, the bleed valve 33d is open. The three valves 33b, 33c, 33d are contained and disposed in and by a body 16 having an inlet port 19, an outlet port 18a, and a vent port 17 for the inlet valve 33b, outlet valve 33c, and bleed valve 33d, respectively (FIGS. 7–10).

Figure 7:
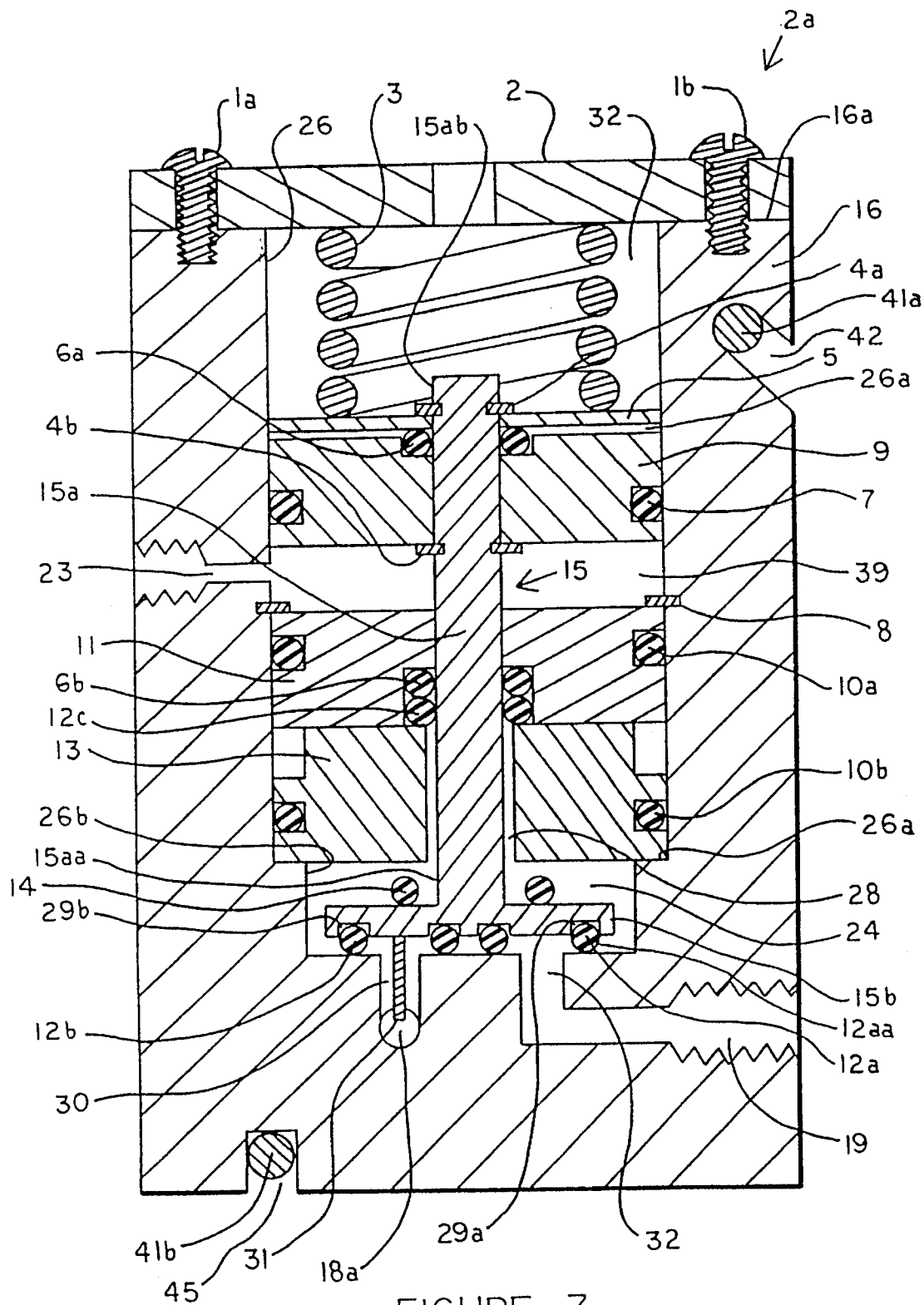
FIG. 7 is a cross-sectional view of the valve manifold shown in FIG. 4, taken along the cutting line 7—7.
Figure 10:
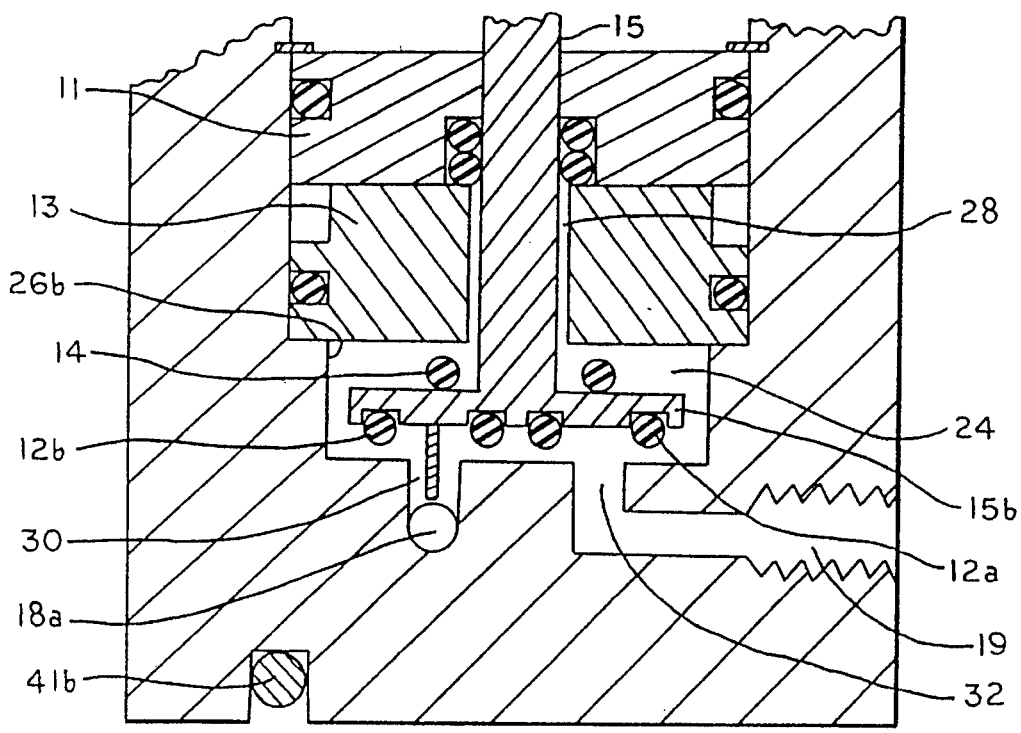
FIGS. 9 and 10 are portions of the cross-sectional view of the valve manifold shown in FIG. 7.
Figure 9:
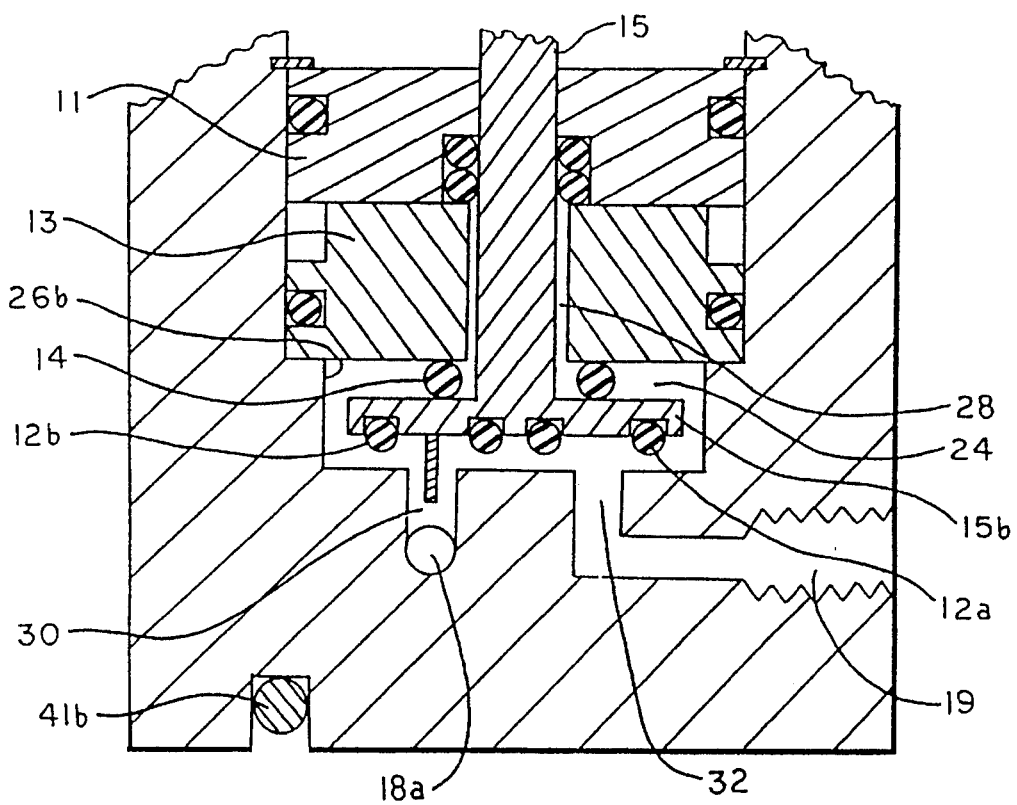

The internal pneumatic actuator comprises a valve poppet 15 having a stem 15a and a flange 15b, first biasing means 3 to urge the popper 15 downward, and second biasing means to force the poppet 15 upward (FIGS. 7, 9, and 10). The first biasing means 3 may be a spring 3, a compressed gas, or other means. Preferably, however, the first biasing means is a spring 3 housed in a chamber 32. The second biasing means is preferably a compressed gas; it is stronger than the first biasing means 3, and prevails when the two are in opposition.

The three valves 33b, 33c, 33d and the pneumatic actuator are disposed within a cavity 26 in the body 16. (FIG. 7.)

When the poppet 15 is in its extreme lower position (FIG. 7), in response to the first biasing means 3 and in the absence of the second biasing means, the sample inlet and outlet valves 33b, 33c are in a closed or blocked configuration, and the bleed valve 33d is open. When the popper 15 is in its extreme upper position (FIG. 9), in response to the second biasing means, the inlet and outlet valves 33b, 33c are open, and the bleed valve 33d is closed. During transition between these two extreme positions, which is momentary, all three valves 33b, 33c, 33d are open (FIG. 10).

It will be understood that the portion of the cavity 26 providing the second biasing means may be maintained at a pressure substantially above atmospheric, even "in the absence of the second biasing means." Such a condition may indeed be beneficial, in order to prevent fugitive fluid emission from the modular body 16. It is therefore necessary, as stated above, that the second biasing means be understood and is herein defined as a pressure sufficient to overcome the first biasing means.

Preferably, the valves 33b, 33c, and 33d comprise flat-face sealing means. Even more preferably, the valves 33b, 33c, and 33d include O-rings (FIGS. 7, 9, and 10).

Figure 8:
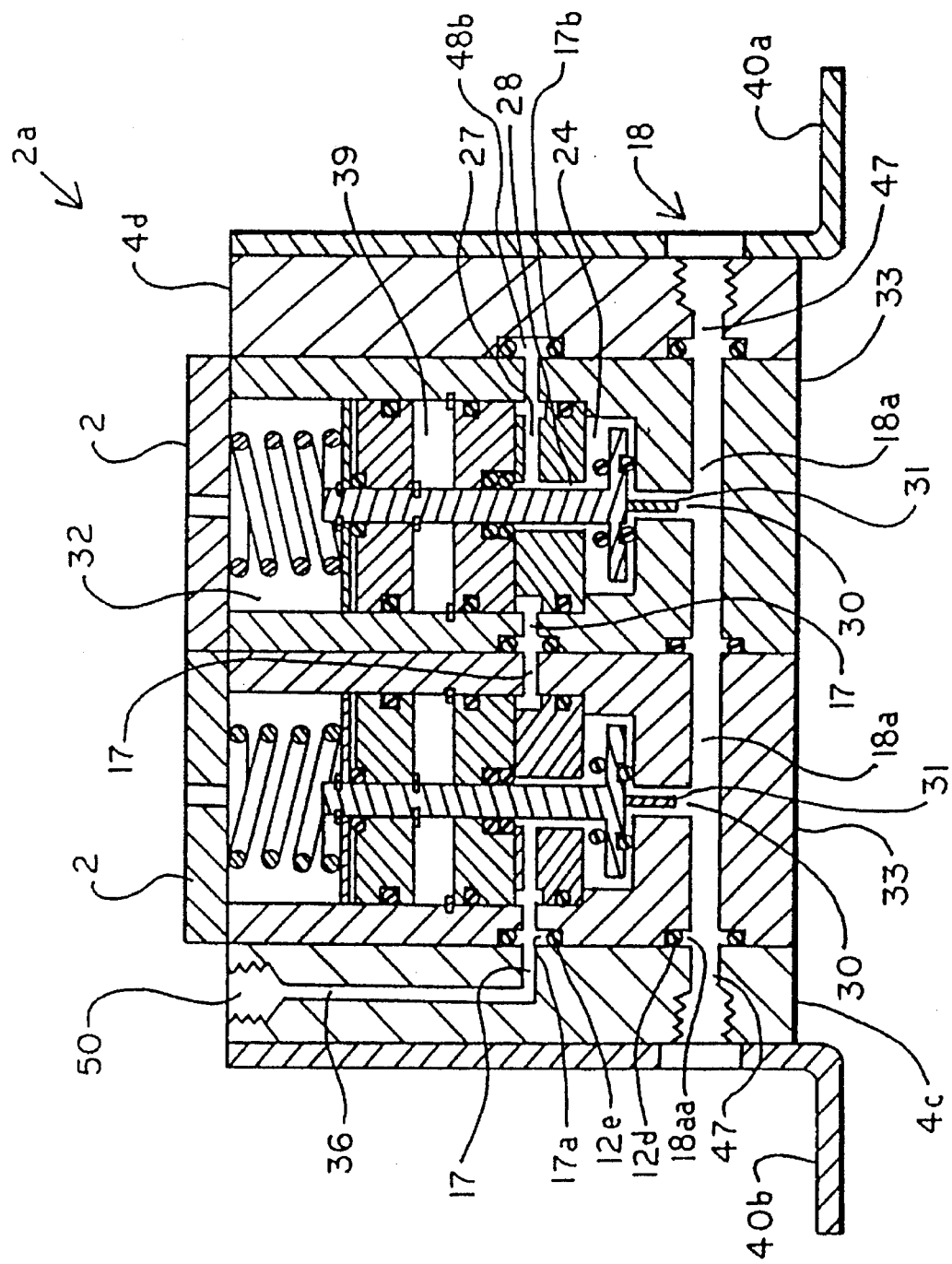
FIG. 8 is a cross-sectional view of the valve manifold shown in FIG. 4, taken along the cutting line
Figure 12:
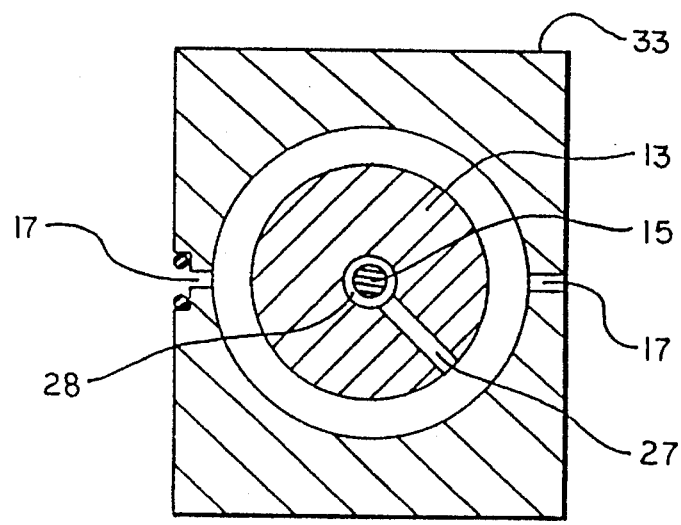
FIG. 12 is a cross-sectional view of the manifold shown in FIG. 4, taken along the cutting line 12—12.

More specifically, a seal-plug bottom part 13 is positioned on a shoulder 26a formed by a reduction of cross-sectional area at the lower end 26b of the cavity 26. (FIGS. 7, 9 and 10.) An O-ring 10b seals the outer surface of the seal-plug bottom part 13 to the inner surface of the cavity 26. A seal-plug top part 11 is disposed over the seal-plug bottom part 13. An O-ring 10a seals the outer surface of the seal-plug top part 11 to the inner surface of the cavity 26. A snap ring 8 retains the seal-plug top part 11 and seal-plug bottom part 13 in a fixed position. The popper 15, comprising a stem 15a and flange 15b, extends axially within the cavity 26. Grooves 29a and 29b in the lower surface of the poppet 15 retain O-rings 12a and 12b. An alignment pin 31 disposed in a passageway 30 maintains axial alignment of the O-ring 12a with a passageway 32 and of O-ring 12b with the passageway 30. A portion 12aa of the O-ring 12a which extends beyond its retaining groove 29a, when forced against the lower surface of a first compartment 24 and in axial alignment with the passageway 32, forms the sample inlet valve 33b which either blocks or permits fluid communication between a sample inlet passageway 19, the passageway 32, and the first compartment 24. In a similar manner, the O-ring 12b forms the sample outlet valve 33c which blocks or permits fluid communication between the outlet passageway 18a, the passageway 30, and the first compartment 24. An O-ring 14 axially disposed around the lower end 15aa of the poppet stem 15a, the upper surface of the poppet flange 15b, and the lower surface of the seal-plug bottom part 13 forms the bleed valve 33d which blocks or permits fluid communication between the first compartment 24 and passageways 28, 27, and 17. (FIGS. 7, 8, and 12.)

The width of the grooves 29a and 29b is from about seventy-five to about ninety-five percent of the width of the O-rings 12a and 12b, respectively. Preferably, the width of the grooves 29a and 29b is from about eighty to about ninety percent of the width of the O-rings 12a and 12b, respectively. Even more preferably, the O-rings 12a and 12b are made of an elastomer having a hardness of from about sixty-five to about seventy-five durometer units, as measured on a Shore "A" gauge, and the depth of the grooves 29a and 29b is from about eighty-seven to about ninety-one percent of the width of the O-rings 12 and 12b, respectively.

The valve popper 15 is normally maintained in the extreme lower position (FIG. 7) by the downward force of the compression return spring 3 applied to the popper stem 15a via an actuator washer 5, actuator piston 9, and an E-ring 4b.

A second compartment 39 comprises the middle portion of the cavity 26. The second compartment 39 is formed by the upper flat surface of the seal-plug top part 11 and the lower flat surface of the piston 9. When the second compartment 39 is pressurized by an external pneumatic source (not shown) of sufficient pressure via a passageway 23, an upward force resulting from the pneumatic pressure applied to the lower surface of the piston 9 overcomes the downward force applied by the compression return spring 3, and lifts the poppet 15 to its extreme upper position (FIG. 9). The popper 15 is in the intermediate position shown in FIG. 10 for only a very short period of time while in transit between the two extreme positions.

O-rings 6b and 12c provide a dynamic seal between the plug-seal top part 11 and the popper stem 15a, thereby ensuring fluid isolation at any position of the stem 15a between the passageway 28 and the second compartment 39.

The piston 9 and washer 5 are axially disposed and retained on the upper portion 15ab of the popper 15 by E-rings 4a and 4b. The O-ring 6a, retained by the washer 5 and axially disposed in a third compartment 26a formed by the upper surface of the piston 9 and the lower surface of the washer 5, provides fluid isolation between the second compartment 39 and a fourth compartment 32, in which the spring 3 is disposed, and which is referenced to (equilibrated with) the atmosphere. The fourth compartment 32 is formed by the lower surface of a cover 2 and the upper surface of the washer 5. An O-ring 7 provides a dynamic seal between the piston 9 and the inside wall of the cavity 26. The cover 2, held to the top 16a of the body 16 screws 1a and 1b, retains compression spring 3 (FIG. 7).

In a second embodiment (FIGS. 3, 4 and 8), the present invention provides a stream-selection valve manifold 2a for a process analyzer. The manifold 2a comprises: (a) a plurality of pneumatic valve modules 33 joined side-by-side, (b) first and second end plates 4c and 4d, and (c) first and second mounting brackets 40a and 40b. The passageway 18a in each valve module 33 is in alignment with the passageways 18a of adjacent valve modules 33 in the manifold 2a. The first and second end plates 4c and 4d, which are in fluid communication with the passageways 18a of adjacent modules 33, provide means for external fluid communication to a single common passageway 18 formed by the outlet passageways 18a of the individual modules 33.

Figure 3:
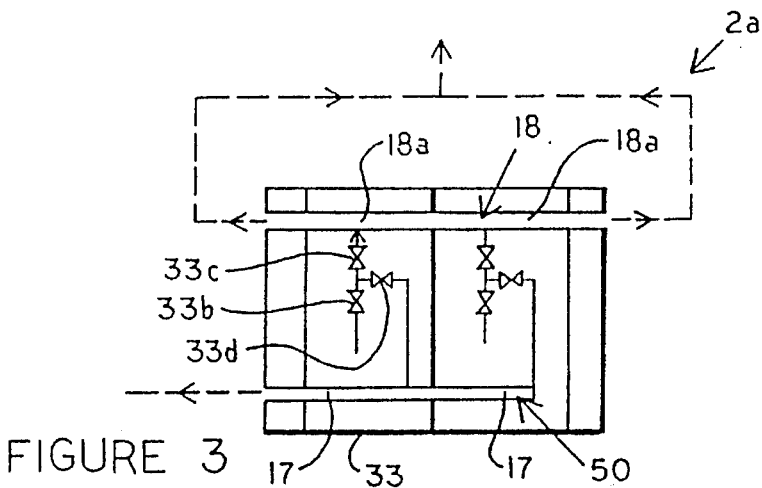
FIG. 3 is a schematic representation of a first embodiment of a stream-selection valve manifold for a process analyzer, made in accordance with the principles of the present invention.

An O-ring 12d (FIG. 8) in a gland 18aa at the end of each module's 33 passageway 18a provides a fluid seal with the passageway 18a of adjacent modules 33 and/or the end plates 4c, 4d. The passageways 17 in the valve modules 33 are joined and sealed with an O-ring 12e in a gland 17a to form a common vent passageway 36 which terminates as a threaded opening 50 in the end plate 4c. The passageway 17 is closed at the end plate 4d by an O-ring 17b in a gland 48b (FIGS. 3 and 8).

Figure 4:
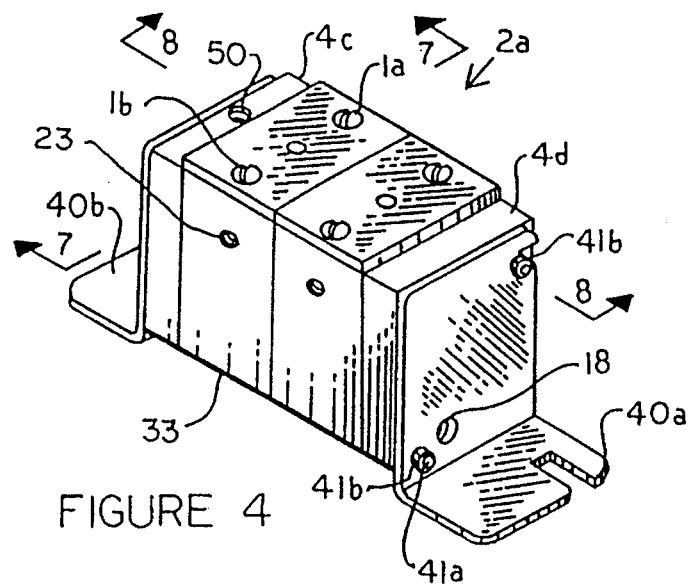
FIG. 4 is an isometric view of the stream-selection valve manifold shown schematically in FIG. 3.
Figure 11:
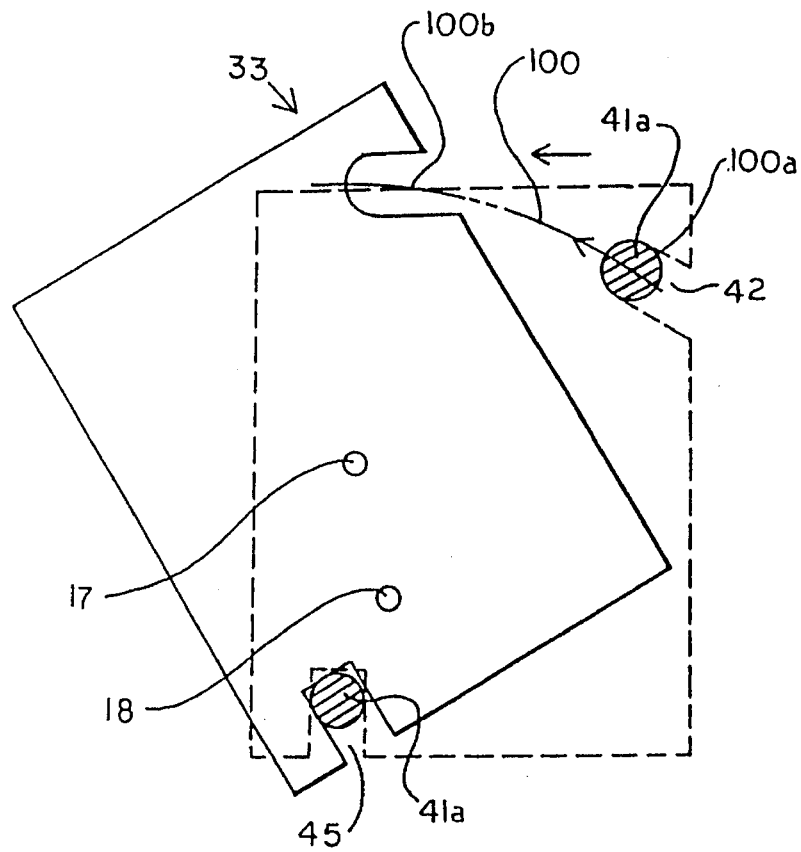
FIG. 11 is a schematic representation showing the removal of a valve module from the stream-selection valve manifold shown in FIGS. 3 and 4.

Mounting is facilitated by the use of mounting brackets 40a and 40b (FIGS. 4 and 8). The entire manifold 2a is held together by threaded rods 41a and nuts 41b. By loosening a first nut 41b at one end of a first threaded rod 41a, a valve module 33 can be removed by rotating it along a path 100 from a first point 100a to a second point 100b about the first threaded rod 41a disposed in a first slot 45. (FIG. 11.) After the valve module 33 has been rotated sufficiently (100b) to clear a second slot 42 from a second threaded rod 41a disposed in a second slot 42, the module 33 can be removed from the manifold 2a. (FIGS. 4 and 11.) When a module 33 is thus removed, the remaining modules 33 and the end plates 4c, 4d remain assembled. Thus the construction of the manifold 2a permits rapid replacement of one or more of the valve modules 33 in the field.

The passageways 18a of the individual valve modules form a common passageway 18 (FIGS. 1 and 3) to an analyzer (not shown). This common passageway 18 occupies a very small volume, and is easy to purge out. The passageway 18 is straight and smooth, has a regular surface, and has no "dead volume" or empty space, thereby significantly reducing the time required for sample flow (purging) before all residual fluid from a previously-selected sample stream is displaced. In a preferred embodiment, the width of the passageway 18 is from about 0.06" to about 0.08". The volume of each passageway 18a in each valve module 33 is from about 0.06 to about 0.08 cubic centimeters; yet the passageways 18a and 18 are not restrictive of fluid flow. The valve module $C_v$ is 0.05. The passageways 18a are located in very close proximity to the outlet valves 33c. The passageway 30, which connects the outlet valve 33c to the passageway 18a, is preferably from about 0.045" to about 0.055" in length. (FIGS. 7, 9, and 10.) The passageway 18a has no "dead" or unpurged space; hence it purges out cleanly and quickly when serving as a conduit for fluid communication in the manifold 2a. (FIG. 8.) Internal passageways 36 and 47 (FIG. 8) of the end plates 4c and 4d, respectively, are also approximately 0.07" in width, and are also constructed without "dead" or unpurged space. Hence the common passageway 18 servicing the entire manifold 2a has a very small volume and no dead space.

When a valve module 33 is actuated and the block valves 33b, 33c are opened, sample fluid from that module flows into the common passageway 18 and out of both end plates 4c, 4d. (FIGS. 4 and 8.) The two flow paths may either be joined external to the manifold 2a, or they may remain divided, with fluid flowing from one of the end plates to vent or bypass, and fluid flowing from the other end plate routed to an analyzer. This pattern of fluid flow ensures that the entire common passageway 18 is adequately purged, thereby significantly reducing the number of fittings as well as the labor and time required for assembling the valve manifold 2a.

Figure 2:
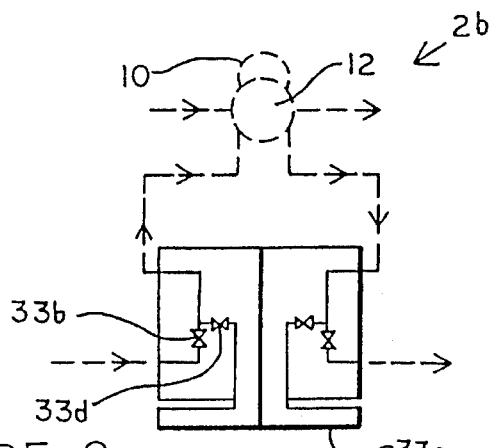
FIG. 2 is a schematic representation of as shutoff and atmospheric reference vent for a process gas chromatograph, made in accordance with the principles of the present invention.
Figure 5:
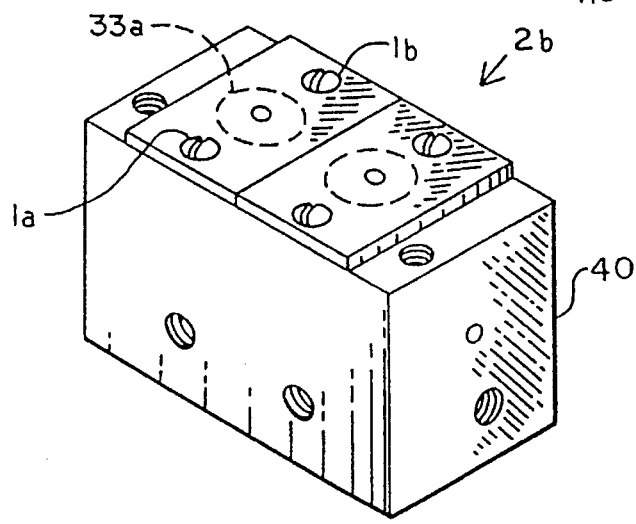
FIG. 5 is an isometric view of the shutoff and atmospheric reference vent shown in FIG. 2.

In a third embodiment (FIGS. 2 and 5), the invention provides a shutoff and atmospheric reference vent 2b for a process gas chromatograph (not shown). By removing the O-ring 12b from the popper 15 (FIGS. 7, 9, and 10) in each of two valve modules 33, and arranging the modified modules 33a as shown, there results a sample shutoff and atmospheric reference vent valve arrangement useful for blocking sample fluid from the sample loop 10 of the injection valve 12 of a gas chromatograph (not shown). The two valve modules 33a are housed in a flow-through modular body 40.

Figure 6:
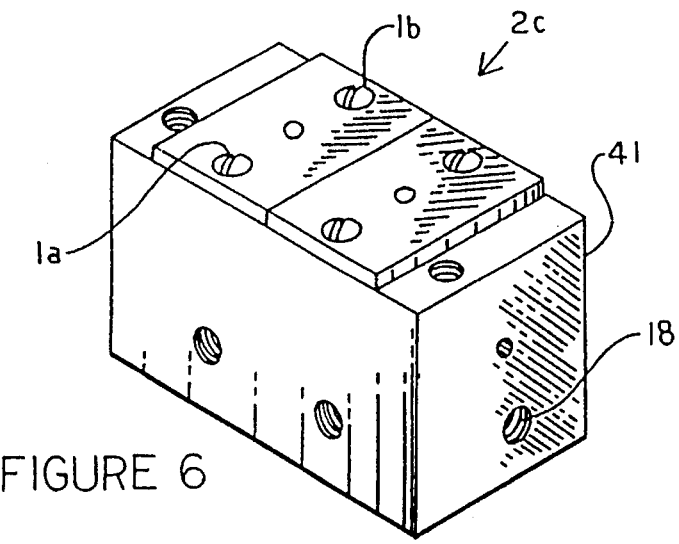
FIG. 6 is an isometric view of the second embodiment of a stream-selection valve manifold for a process analyzer shown schematically in FIG. 1.

In a fourth embodiment, the invention 2c (FIGS. 1 and 6) provides a stream-selection valve manifold comprising two valve modules 33 disposed side-by-side in a flow-through modular body 41, thereby eliminating the need for the end plates 4c, 4d and the mounting brackets 40a, 40b of the manifold 2a (FIGS. 4 and 8).

In a fifth embodiment the present invention provides a single block-and-bleed valve module for selectively controlling fluid flow.

Figure 13:
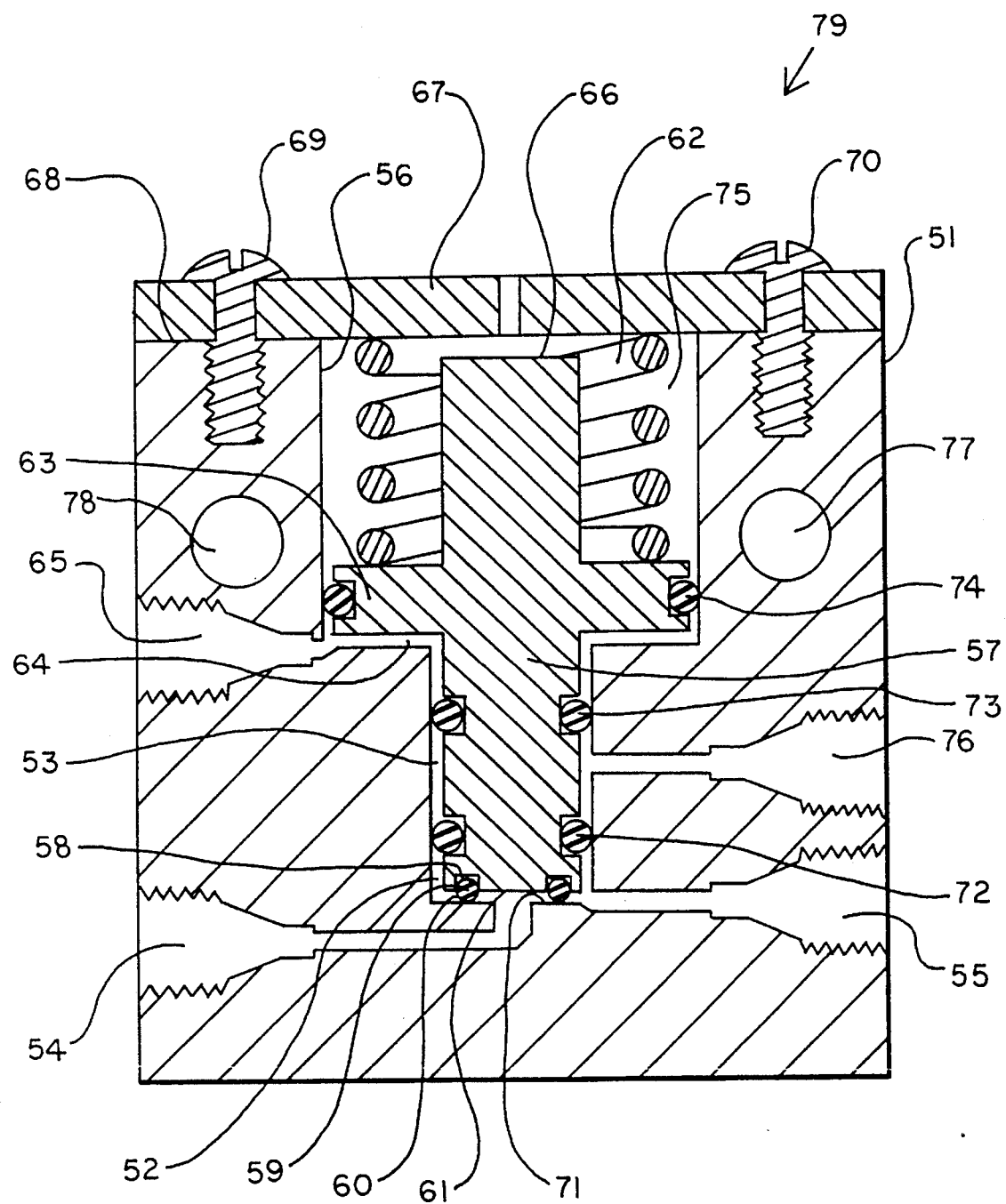
FIG. 13 is a vertical cross-sectional view of a single block-and-bleed valve module, made in accordance with the principles of the present invention.

Reference is made to FIG. 13, which shows that the single block-and-bleed module 79 is comprised of a block valve, a sample fluid compartment 52, a vent compartment 53, and an internal pneumatic actuator, all of which are disposed within a cavity 56 in a body 51. The block valve is constructed and arranged so that, when closed, fluid communication is blocked between an inlet passageway 54 and the sample fluid compartment 52. In the "open position" of the block valve, an inlet passageway 54, the sample fluid compartment 52, and an outlet passageway 55 are in fluid communication. The outlet passageway 55 and the sample fluid compartment 52 are in fluid communication in both the "open" and "closed" positions of the block valve.

A popper 57 is axially disposed within the cavity 56. A groove 58 in the lower surface 61 of the popper 57 retains a first O-ring 59 in axial alignment with the passageway 54. A portion 60 of the O-ring 59 which extends beyond the groove 58, in combination with the lower surface 71 of the compartment 52, forms the block valve which, when the portion 60 of the O-ring 59 is forced against the lower surface 71 of the compartment 52 and in axial alignment with the passageway 54, closes the valve. The passageway 54 provides means for fluid communication from the environment external of the body 51 to the sample-fluid compartment 52. The passageway 55 provides means for fluid communication from the sample-fluid compartment 52 to the environment external of the valve body 51. The function of the passageways 54 and 55 can be reversed without altering the function of the valve module 79.

An actuator piston 63 is formed by an enlargement of the width of the popper 57 near the longitudinal center of the popper 57. The poppet 57 is normally maintained in the extreme lower position shown in FIG. 13 by the downward force of a compression return spring 62 applied to the actuator piston 63.

The internal pneumatic actuator comprises the actuator piston 63 and an actuator compartment 64. When an external source of sufficient pneumatic pressure is supplied to the actuator compartment 64 via a passageway 65, an upward force resulting from the pneumatic pressure applied to the lower surface of the actuator piston 63 overcomes the downward force applied by the compression spring 62, and lifts the popper 57 to its extreme upper position. The upper surface 66 of the popper 57 contacting cover 67 limits the travel of the popper 57 in its extreme upper position. The cover 67 is held to the top 68 of the body 51 by screws 69 and 70. The portion 60 of the O-ring 59 contacting the lower surface 71 of the compartment 51 limits the travel of the popper 57 in its extreme lower position.

The block valve is in a closed mode when the popper 57 is at its extreme lower position, and in an open mode when the poppet is at its extreme upper position.

The compartment 52 is formed by the annulus be%ween the popper 57 and the inner surface of the cavity 56, from the lower surface 71 of the cavity 56 to a second O-ring 72.

The vent compartment 53 is formed by the annulus between the popper 57 and the inner surface of the cavity 56, from the second O-ring 72 to a third O-ring 73.

The actuator compartment 64 is formed by the annulus between the poppet 57 and the inner surface of the cavity 56, from the third O-ring 73 to a fourth O-ring 74. The return spring 62 is housed in a spring compartment 75 formed in the upper portion of the cavity 56 between the fourth O-ring 74 and the lower surface of the cover 67.

A passageway 76 provides fluid communication between the vent compartment 53 and the environment external of the body 51. The end of the passageway 76 terminating at the external surface of the valve body 51 is normally in fluid communication, by tubing or piping means, with an area (not shown) suitable for the safe disposal of sample fluids contained within the sample-fluid compartment 52. Pressure within the passageway 76 and the compartment 53 is normally maintained at a level equal to or lower than that of the sample-fluid compartment 52, the passageway 54, the passageway 55, and the compartment 64.

The O-rings 72, 73, and 74 provide fluid sealing between the compartments 52, 53, 64, and 75. Should the O-ring 72 fail, resulting in sample fluid from the sample-fluid compartment 52 entering the vent compartment 53, the passageway 76 will conduct this fluid to the safe-disposal area referred to above.

In a similar manner, pneumatic-supply gas entering the vent compartment 53 as a result of breaching the O-ring 73, should that O-ring fail, would also be conducted to the external safe-disposal area in fluid communication with the passageway 76.

These characteristics provide a "bleed" feature which ensures that there will not be fugitive emission of sample fluids or pneumatic gas from the valve module 79 to contaminate the surrounding atmosphere, thereby providing a solution to this problem which has continued to plague the prior art.

Mounting holes 77 and 78 provide convenient means for mounting the valve module 51.

The flat-face sealing structure of each valve is very tolerant of scratching of and/or irregularities in the sealing means, of abrasive particulates which may be present in the sample fluid, and even of minor structural damage to the sealing means.

While certain specific embodiments and details have been described in order to illustrate the present invention, it will be apparent to those skilled in the art that many modifications can be made therein without departing from the basic concept and scope of the invention.

I claim:

1. A valve module for use with other similar modules to form a variety of different valve manifold assemblies comprising:

a) a valve body including a first pair of spaced lateral exterior side walls;

b) a valve chamber in the body;

c) a first flow passageway extending through the body between the first pair of lateral exterior side walls;

d) a second flow passageway extending between the first pair of lateral exterior side walls in parallel flow relationship with said first flow passageway;

e) separate connecting flow passages joining the first flow passageway and the second flow passageway to respective first and second valve seats in the valve chamber;

f) a valve means in the valve chamber movable between a first position wherein the first valve seat is closed to a second position wherein the first valve seat is opened and the second valve seat is closed; and, g) actuating means for moving the valve means between the first and second positions.

2. A valve module as defined in claim 1 including a third passageway extending from the exterior of the valve body, a third valve seat in the valve chamber and said valve means operable to open and close the third valve seat simultaneously with the first valve seat.

3. A valve module as defined in claim 2 wherein the valve means in the valve chamber comprises a poppet member having a first side face carrying first and second seal means for cooperating with the first and second valve seats and a second side face carrying a third seal means for cooperating with the third valve seat.

4. A valve module as defined in claim 3 wherein the first and second side faces of the poppet member are generally perpendicular to the path.

5. A valve module as defined in claim 3 wherein the valve chamber has first and second opposed end walls with the first and second seats located in the first end wall and the third seat located in the second end wall.

6. A valve module as defined in claim 5 wherein the poppet member includes an operating stem portion extending through the second end wall centrally of the third seat.

7. The valve module of claim 5 wherein said valve chamber is defined by a cavity which extends inwardly of the body and wherein the second end wall is defined by a plug member which is sealingly received in the cavity.

8. The valve module of claim 6 wherein the stem portion extends axially of the cavity and wherein the third seal means is disposed about the poppet member stem portion.

9. The valve module of claim 8 including an actuator piston joined to the poppet member stem portion and movable axially of the cavity.

\* \* \* \* \*